United States Patent [19]

Srivastava et al.

[11] Patent Number: 5,654,412
[45] Date of Patent: Aug. 5, 1997

[54] PROCESSES FOR THE SYNTHESIS OF SIALYL LEWIS$^x$ COMPOUNDS

[75] Inventors: Om Srivastava; Jonathan M. Gregson, both of Edmonton, Canada

[73] Assignee: Glycomed Incorporated, Alameda, Calif.

[21] Appl. No.: 657,456

[22] Filed: May 29, 1996

[51] Int. Cl.$^6$ .............................. C07H 15/00; C07H 1/00
[52] U.S. Cl. ........................................ 536/18.5; 536/55.3
[58] Field of Search ..................... 536/18.5, 55.3

[56] References Cited

U.S. PATENT DOCUMENTS

| | | | |
|---|---|---|---|
| 5,079,353 | 1/1992 | Ratcliffe et al. | 536/53 |
| 5,426,178 | 6/1995 | Laine et al. | 536/1.11 |
| 5,470,843 | 11/1995 | Stahl et al. | 514/61 |
| 5,559,103 | 9/1996 | Gaeta et al. | 514/54 |
| 5,580,858 | 12/1996 | Ippolito et al. | 514/25 |

OTHER PUBLICATIONS

Amvam–Zollo, et al., *Carbohydr. Res.*, 150:199–212 (1986).
Chernyak, et al., *Carbohydr. Res.*, 128:269–282 (1984).
Dahmen, et al., *Carbohydr. Res.*, 118:292–301 (1983).
Ekberg, et al., *Carbohydr. Res.*, 110:55–67 (1982).
Fernandez–Santana, et al., *J. Carbohydr. Chem.*, 8:531–537 (1989).
Lee, et al., *Carbhydr. Res.*, 37:193–201 (1974).
Paulsen, et al., *Carbohydr. Res.*, 104:195–219 (1982).
Rana, et al., *Carbohydr. Res.*, 91:149–157 (1981).
Sleytr, et al., *Arch. Microbiol.*, 146:19–24 (1986).
Smith and Zoila, *Immunology*, 58:245–250 (1986).

*Primary Examiner*—Kathleen K. Fonda
*Attorney, Agent, or Firm*—Burns, Doane, Swecker & Mathis, L.L.P.

[57] ABSTRACT

Disclosed are processes for the chemical synthesis of sialyl Lewis$^x$-Y compounds where Y is —OH, —NHR, —SH, —SR or —OR, and R is an aglycon of at least one carbon atom.

12 Claims, 3 Drawing Sheets

PROCESSES FOR THE SYNTHESIS OF SIALYL LEWIS$^x$ COMPOUNDS

BACKGROUND OF THE INVENTION

Field of the Invention

This invention is directed to processes for the chemical synthesis of sialyl Lewis$^x$-Y compounds where Y is —OH, —NHR, —SH, —SR and —OR and R is an aglycon of at least one carbon atom. In particular, this invention is directed to a convergent synthesis of sialyl Lewis$^x$-Y compounds by the assembly of two disaccharide pairs and subsequent coupling of these pairs into sialyl Lewis$^x$-Y.

Also disclosed are several novel compounds related to sialyl Lewis$^x$-Y including 8-methoxycarbonyloctyl (5-acetamido-3,5-di-deoxy-α-D-glycero-D-galacto-2-nonulopyranosylonic acid) -(2→3)-O-β-galactopyranosyl-(1→4)-O-[α-L-fucopyranosyl-(1→3-O-]-2-benzamido-2-deoxy-β-D-glucopyranoside.

REFERENCES

The following references are cited in this application as superscript numbers at the relevant portion of the application:

[1] Ratcliffe, et al., U.S. Pat. No. 5,079,353, issued Jan. 7, 1992, for SIALIC ACID GLYCOSIDES, ANTIGENS, IMMUNOADSORBENTS, AND METHODS FOR THEIR PREPARATION.

[2] Jiang, et al., U.S. patent application Ser. No. 07/848,223, filed Mar. 9, 1992, for CHEMICAL SYNTHESIS OF GDP-FUCOSE.

[3] Ekberg, et al., Carbohydr. Res., 110:55–67 (1982).

[4] Dahmen, et al., Carbohydr. Res., 118:292–301 (1983).

[5] Rana, et al., Carbohydr. Res., 91:149–157 (1981).

[6] Amvam-Zollo, et al., Carbohydr. Res., 150:199–212 (1986).

[7] Paulsen, et al., Carbohydr. Res., 104:195–219 (1984).

[8] Chernyak, et al., Carbohydr. Res., 128:269–282 (1984).

[9] Fernadez-Santana, et al., J. Carbohydr. Chem., 8:531–537 (1989).

[10] Lee, et al., Carbohydr. Res., 37:193 et seq., (1974).

[11] Ippolito, et al., U.S. patent application Ser. No. 07/988,518, filed Dec. 9, 1992, for TIME DEPENDENT ADMINISTRATION OF OLIGOSACCHARIDE GLYCOSIDES FOR REDUCTION OF INFLAMMATION ARISING FROM RESPONSE TO AN ANTIGEN.

[12] Venot, et al., U.S. patent application Ser. No. 08/326,745, filed Oct. 20, 1994 for MODIFIED SIALYL LEWIS$^x$ COMPOUNDS.

[13] Smith and Zoila, Immunology, 58:245 (1986).

[14] Sleytr, et al., Arch. Microbiol., 146:19 (1986).

The disclosure of each of the above-referenced publications and patent applications are herein incorporated by reference in their entirety to the same extent as if each individual publication, patent or patent application was specifically and individually indicated to be incorporated by reference in its entirety.

STATE OF THE ART

Sialyl Lewis$^x$-Y glycosides and derivatives thereof have been disclosed as possessing mammalian immunosuppressive and tolerogenic properties[11,13]. The art also discloses that sialyl Lewis$^x$ compounds possess anti-inflammatory properties by virtue of its binding to endothelium leukocyte adhesion molecule-1 (ELAM-1). Still further the art discloses that sialyl Lewis$^x$-Y compounds are useful in the generation of antibodies which can then be used to detect, for example, cancer in humans[1].

Notwithstanding its many uses, the art has not produced a convenient synthesis for sialyl Lewis$^x$-Y compounds. Enzymatic methods for the synthesis of sialyl Lewis$^x$-Y compounds require the use of sialyltransferases and/or fucosyltransferases as well as the synthesis of CMP-sialic acid and/or GDP-fucose[2] each of which constrains the overall synthetic method. Likewise, while the total chemical synthesis of sialyl Lewis$^x$-Y was reported by Ratcliffe, et al.[1], the art reports that this is cost prohibitive.

SUMMARY OF THE INVENTION

This invention is directed to novel processes for the overall chemical synthesis of sialyl Lewis$^x$-Y compounds and derivatives thereof modified at the 2-position of the N-acetyl unit which processes involve a convergent synthesis via two disaccharide subcomponents. Specifically, in the methods of this invention, a 3-fucosyl-N-acetylglucosamine-Y disaccharide structure or a derivative thereof protected at all of the hydroxyl groups except the 4-position of the N-acetylglucosamine is coupled to a 2-sialyl-galactosyl disaccharide structure which has a leaving group at the 1-position of the galactosyl group and which has all of its hydroxyl groups protected.

This convergent synthesis provides for highly efficient methods for preparing sialyl Lewis$^x$-Y compounds wherein the number of manipulations is kept to a minimum and yield is improved.

Accordingly, in one of its process aspects, this invention is directed to a process for the preparation of sialyl Lewis$^x$-Y compounds which process comprises:

(a) contacting a compound of the formula I with at least a stoichiometric amount of a compound of the formula II under conditions to provide for a compound of the formula III:

III wherein each X is independently selected from the group consisting of —NHB and —NHC(O)$R^1$ where $R^1$ is alkyl of from 1 to 6 carbon atoms, alkaryl of from 7 to 12 carbon atoms, aryl of from 6 to 10 carbon atoms, alkheteroaryl, and heteroaryl; Y is selected from the group consisting of —OB, —OR, —SB, —SR, —NHR; each B is independently a removable blocking group; B' is a removable blocking group selected from the group consisting of benzyl and substituted benzyl; and L is a leaving group;

(b) removing all of the B and B' removable blocking groups to provide for a compound of formula IV:

IV or a salt thereof wherein L and X are as defined above and Y' is selected from the group consisting of —OH, —OR, —SH, —SR, and —NHR, and (c) optionally converting the compound produced in (b) above to a pharmaceutically acceptable salt.

DETAILED DESCRIPTION OF THE PREFERRED EMBODIMENTS

This invention is directed to processes for the chemical synthesis of sialyl Lewis$^x$-Y compounds. However, prior to discussing this invention in further detail, the following terms will be defined.

DEFINITIONS

As used herein, the following terms have the definitions given below:

The term "aglycon of at least one carbon atom" refers to non-saccharide containing residues having at least one carbon atom. Preferably, the aglycon has from 1 to about 20 carbon atoms and more preferably is selected from the group consisting of —(A)—Z wherein A represents a bond, an alkylene group of from 2 to 10 carbon atoms, and a moiety of the form —(WG)$_n$— wherein n is an integer equal to 1 to 5; W is a straight or branched chain alkylene group of from 2 to 10 carbon atoms optionally substituted with 1 to 3 substituents selected from the group consisting of aryl of 6 to 10 carbon atoms and aryl of from 6 to 10 carbon atoms substituted with from 1 to 3 substituents selected from the group consisting of amino, hydroxyl, halo, alkyl of from 1 to 4 carbon atoms and alkoxy of from 1 to 4 carbon atoms; G is selected from the group consisting of a bond, O, S and NH; and Z is selected from the group consisting of hydrogen, methyl, phenyl, nitrophenyl and, when G is not oxygen, sulphur or nitrogen and when A is not a bond, then Z is also selected from the group consisting of —OH, —SH, —NH$_2$, —NHR$^6$, —N(R$^6$)$_2$, —C(O)OH, —C(O)OR$^6$, —C(O)NH—NH$_2$, —C(O)NH$_2$, —C(O)NHR$^6$, —C(O)N(R$^6$)$_2$, and —OR$^7$ wherein each R$^6$ is independently alkyl of from 1 to 4 carbon atoms and R$^7$ is an alkenyl group of from 3 to 10 carbon atoms.

Numerous aglycons are known in the art. For example, an aglycon comprising a para-nitrophenyl group (i.e., R=—C$_6$H$_4$(p)NO$_2$) has been disclosed by Ekberg, et al.[3] At the appropriate time during synthesis, the nitro group is reduced to an amino group which can be protected as N-trifluoroacetamido. When desired, the trifluoroacetamido group is removed thereby unmasking the amino group.

An aglycon containing sulfur is disclosed by Dahmen, et al.[4] Specifically, the aglycon is derived from a 2-bromoethyl group which, in a substitution reaction with thionucleophiles, has been shown to lead to aglycons possessing a variety of terminal functional groups such as —CH$_2$CH$_2$SCH$_2$CO$_2$CH$_3$ and —CH$_2$CH$_2$SC$_6$H$_4$(p)NH$_2$.

Rana, et al.[5] discloses a 6-trifluoroacetamidohexyl aglycon [—(CH$_2$)$_6$NHCOCF$_3$] in which the trifluoroacetamido protecting group can be removed unmasking the primary amino group.

Other exemplifications of known aglycons include the 7-methoxycarbonyl-3,6-dioxaheptyl aglycon[6] (—CH$_2$CH$_2$)OCH$_2$CO$_2$CH$_3$; the 2-(4-methoxycarbonylbutancarboxamido)ethyl[7] [—CH$_2$CH$_2$NHC(O)(CH$_2$)$_4$CO$_2$CH$_3$]; and the allyl aglycon[8] (—CH$_2$CH=CH$_2$) which, by radical co-polymerization with an appropriate monomer, leads to co-polymers; other allyl linking aglycons[9] are known [e.g., —(CH$_2$CH$_2$O)$_2$CH$_2$CH=CH$_2$]. Additionally, allyl linking arms can be derivatized in the presence of 2-aminoethanethiol[10] to provide for the aglycon of the formula —CH$_2$CH$_2$CH$_2$SCH$_2$CH$_2$NH$_2$. Still other aglycons are illustrated hereinbelow.

Additionally, as shown by Ratcliffe, et al.[1], the R group can be an additional saccharide-OR' or an oligosaccharide-OR' at the reducing sugar terminus (where R' is an aglycon as defined above).

Preferably, the aglycon moiety is a hydrophobic group and most preferably, the aglycon moiety is a hydrophobic group selected from the group consisting of —(CH$_2$)$_8$COOCH$_3$, —(CH$_2$)$_5$OCH$_2$CH=CH$_2$ and —(CH$_2$)$_8$CH$_2$OH.

The term "pharmaceutically acceptable salts" include the pharmaceutically acceptable addition salts of sialyl Lewis$^x$-Y compounds or derivatives thereof which salts are derived from a variety of organic and inorganic counter ions well known in the art and include, by way of example only, sodium, potassium, calcium, magnesium, ammonium, tetraalkyl-ammonium, and the like.

The term "removable blocking group" refers to any group which when bound to one or more hydroxyl groups of the galactose, the N-acetylglucosamine, the sialic acid and/or the fucose units used to prepare the sialyl Lewis$^x$-Y derivatives described herein prevents reactions from occurring at these hydroxyl groups and which protecting groups can be removed by conventional chemical and/or enzymatic procedures to reestablish the hydroxyl group. The particular removable blocking group employed is not critical and preferred removable hydroxyl blocking groups include conventional substituents such as benzyl, benzoyl, acetyl, chloroacetyl, benzylidene, t-butylbiphenylsilyl and any other group that can be introduced onto a hydroxyl functionality and later selectively removed by conventional methods in mild conditions compatible with the nature of the product.

The term "leaving group" refers to any conventional leaving group which is readily displaced by nucleophilic attack under mild reaction conditions. Such groups include, by way of example only, imidate, thioglycoside, chloro, bromo, and the like. The particular leaving group employed is not critical. Preferably, the leaving group is either imidate or benzylthioglycoside.

The term "aryl" refers to an aromatic group having a single ring or multiple condensed rings and having from 6 to 10 carbon atoms which structure may be optionally substituted with 1 to 3 substituents selected from alkyl of from 1 to 6 carbon atoms, alkoxy of from 1 to 6 carbon atoms, amino, hydroxyl, cyano, carboxyl, halo, nitro and the like.

The term "heteroaryl" refers to an aromatic heterocyclic group having a single ring or multiple condensed rings and having from 2 to 12 carbon atoms and 1 to 4 heteroatoms selected from oxygen, nitrogen and sulfur within the ring which structure may be optionally substituted with 1 to 3 substituents selected from alkyl of from 1 to 6 carbon atoms, alkoxy of from 1 to 6 carbon atoms, amino, hydroxyl, cyano, carboxyl, halo, nitro and the like.

The terms "alkaryl" and "alkheteroaryl" refers to the groups —R"-Aryl and —R"-Heteroaryl, where aryl group and heteroaryl are as defined above and R" is an alkylene group of from 1 to 6 carbon atoms including straight and branched alkylene groups. Examples of alkaryl and alkheteroaryl groups include benzyl, —CH$_2$CH$_2$φ, and furfuryl.

METHODOLOGY

The processes of this invention involve the synthesis of sialyl Lewis$^x$-Y compounds and derivatives thereof in a convergent synthesis from two disaccharide blocks. The following discussion will illustrate processes for the preparation of these compounds by specific reference to FIG. 1. It is understood, however, that the describe processes are applicable to the synthesis of compounds in addition to that illustrated in FIG. 1 and that this figure is only for illustrative purposes.

Figure 1:
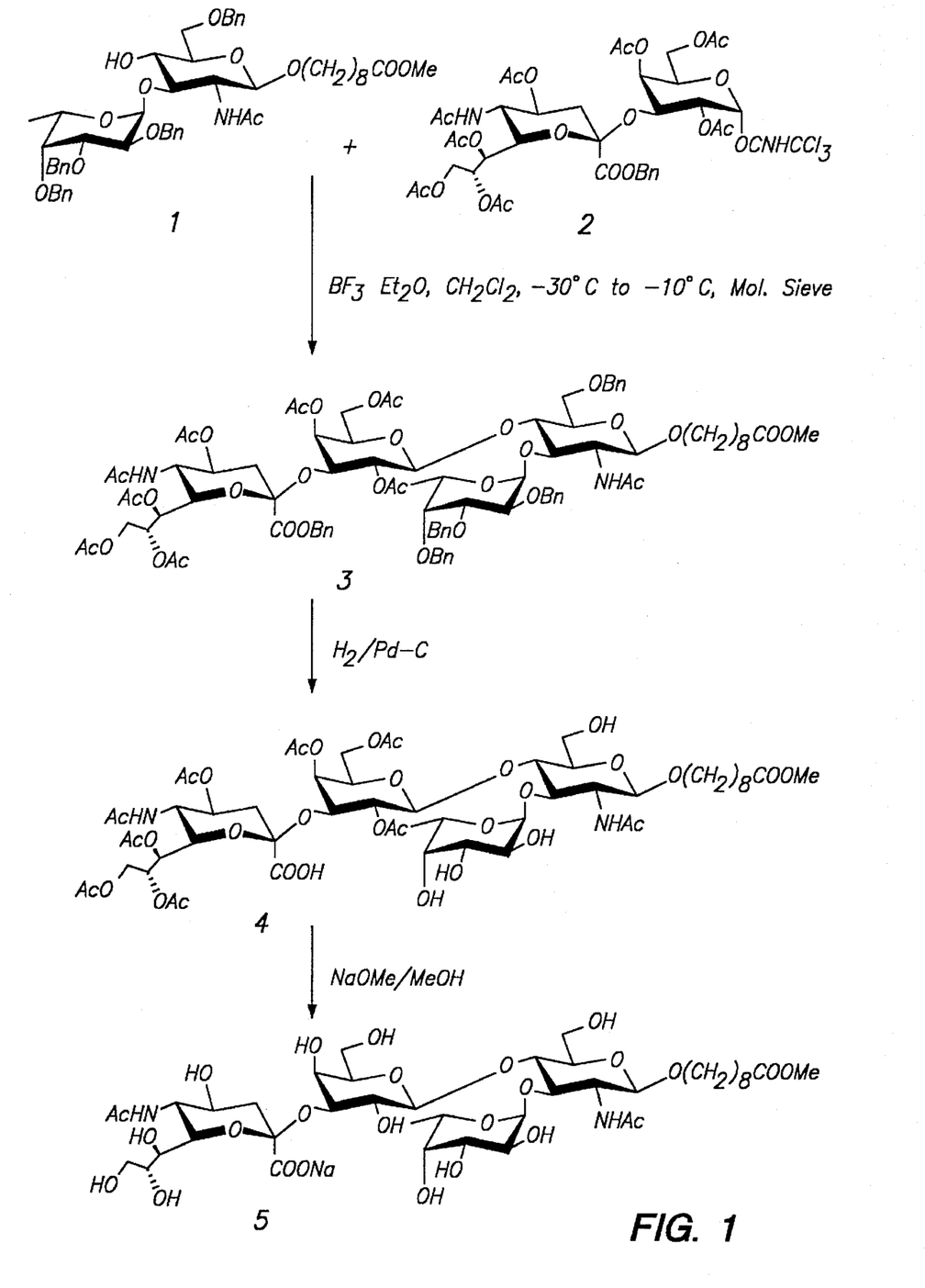
FIG. 1 illustrates a preferred reaction scheme which can be used to obtain the sialyl Lewis$^x$-OR compounds described herein.

Specifically, as shown in FIG. 1, disaccharide 1 is coupled to disaccharide 2 under conditions which result in formation of fully protected tetrasaccharide 3. This reaction is typically conducted by combining a stoichiometric excess of compound 2 with compound 1 in an inert diluent such as chloroform, dichloromethane, diethylether, and the like. The reaction is typically conducted at from about −30° to about 0° C. until reaction completion which typically occurs within 0.5 to about 5 hours.

In a particularly preferred embodiment, approximately 1.2 to about 1.5 equivalents of compound 2 are employed relative to compound 1 in a 1:1 mixture of dichloromethane:ether at a temperature of from −30° to about −10° C. for a period of about 0.5 hours to provide for the fully protected tetrasaccharide structure 3.

Conventional deprotection of compound 3 yields the desired sialyl Lewis$^x$-Y compounds in high yield. As is apparent, the deprotection methods are selected relative to the protecting groups and deprotection is well known in the art.

Alternatively, in compound 1, the N-acetyl group can be replaced by a —NH$_2$ or —NHCO(O)R$^1$ where R$^1$ is alkyl of from 1 to 6 carbon atoms, alkaryl of from 7 to 12 carbon atoms and aryl of from 6 to 10 carbon atoms by merely employing the appropriate starting materials. For example, use of the azido derivative as disclosed by Ratcliffe, et al.[1] with subsequent reduction to the amino can be employed. The amino group can then either be blocked with a removable blocking group or can be converted to —NHC(O)R$^1$ via conventional acylation reactions. Conversion of the azido compound to the amino derivative occurs during an appropriate point in the synthesis which is selected relative to additional reaction steps to be conducted. When such additional reaction steps may unintentionally react with the amino derivative, the amino is typically protected by conventional methods with a removable blocking group. Other derivatives of the 2-position of the N-acetylglucosamine structure are found in Venot, et al.[12]

In FIG. 1, disaccharide 1 and derivatives thereof are described by Srivastava et al., U.S. Ser. No. 08/343,020 which application is incorporated herein by reference in its entirety. Additional Example A below illustrates the synthesis of the specific 8-methoxycarbonyloctyl-2-acetamido-3-O-(2,3,4-tri-O-benzyl-α-L-fucopyranosyl)-6-O-benzyl-2-deoxy-β-D-glucopyranoside identified in FIG. 1 as compound 1.

Disaccharides where Y is —NHR, or —SR are readily prepared during the synthesis of the N-acetylglucosamine monosaccharide merely by substituting a suitable amine or thiol compound for the alcohol employed to prepare the glycoside as described in Srivastava, et al., U.S. Ser. No. 08/343,020. One preferred Y substitutent is the benzamido group.

Also, in FIG. 1, disaccharide 2 and derivatives thereof are described by Ratcliffe et al.[1] which is incorporated herein by reference in its entirety. Alternatively, disaccharide 1 may be prepared by using a thioglycoside leaving group on the sialic acid, e.g., thiobenzyl. The thiobenzyl group is prepared by reacting the peracetylated derivative described in FIG. 2 of Ratcliffe et al. with a stoichiometric excess of benzyl mercaptan (e.g, 2 to 5 equivalents) in dichloromethane using about 1 to 3 equivalents and preferably about 1.5 equivalents of boron trifluoride etherate as a catalyst. This reaction is typically conducted at from about 0° C. to about room temperature and is typically complete within about 10 hours.

The convergent synthesis described above provides for a highly efficient means to prepare sialyl Lewis$^x$-Y compounds. Using the methods of this invention, coupling of the two disaccharides to form the sialyl Lewis$^x$-Y compounds can be conducted in very high yields approaching 90%.

UTILITY

The sialyl Lewis$^x$-Y compounds prepared by the processes described herein are useful in treating inflammation including the inflammatory component of an immune response to an antigen challenge in mammals which have been previously sensitized to that antigen. When employed to treat the inflammatory component of an immune response to an antigen challenge, the sialyl Lewis$^x$-Y compounds and derivatives thereof are preferably administered within one-half the period required for maximal inflammatory response to the antigen challenge[11]. Additionally, when so administered, the sialyl Lewis$^x$-Y compounds and derivatives thereof described herein also induce tolerance to later challenges by the same antigen in the treated mammal.[11]

The sialyl Lewis$^x$-Y compounds described herein are effective in modulating the inflammatory component of such immune responses when administered at a dosage range of from about 0.5 mg to about 50 mg/kg of body weight, and preferably from about 0.5 to about 5 mg/kg of body weight. The specific dose employed is regulated by the particular inflammatory component of the immune response being treated as well as by the judgment of the attending clinician depending upon factors such as the severity of the adverse immune response, the age and general condition of the patient, and the like. Additionally, as is apparent, more active compounds will require less dosing than less active compounds.

The sialyl Lewis$^x$-Y compounds and derivatives thereof are generally administered parenterally, such as intranasally, intrapulmonarily, transdermally and intravenously, although other forms of administration are contemplated.

The sialyl Lewis$^x$-Y compounds are also useful in the generation of antibodies which can then be used to detect, for example, cancer in humans[1].

EXAMPLES

The following examples are set forth to illustrate the claimed invention and are not to be construed as a limitation thereof.

Examples A and B illustrate methods for preparing the starting disaccharide building blocks employed in the convergent synthesis described herein. Examples 1–3 illustrate the synthesis of sialyl Lewis$^x$-O(CH$_2$)$_8$COOCH$_3$ as per this invention and Examples 4–10 illustrate the synthesis of sialyl Lewis$^x$-OH as per this invention.

In these examples, the following abbreviations used therein have the following meanings. If not defined, any abbreviation used below has its generally accepted meaning.

| | |
|---|---|
| °C. | degrees Celcius |
| cm | centimeter |
| d | doublet |
| DBU | 1,8-diazabicyclo[5.4.0]Undec-7-ene |
| DMF | dimethylformamide |
| DTH | delayed type hypersensitivity |
| EDTA | ethylene diamine tetraacetic acid |
| eq. | equivalents |
| g | gram |
| $^1$H-NMR | proton nuclear magnetic resonance |
| h | hours |
| kg | kilogram |
| L | liter |
| m | multiplet |
| M | molar |
| mg | milligram |
| mL | milliliter |
| mmol | millimol |
| PBS | phosphate buffered saline |
| s | singlet |
| t | triplet |
| tlc | thin layer chromatography |
| μg | microgram |
| μL | microliter |

Anberlite IR-120 (H$^+$ form) ion exchange resin available from Rohm & Haas, Philadelphia, Pa.

Iatrobeads were from Iatron Laboratories, Tokyo, Japan.

Additionally, all sugars recited herein are in their pyranose form and are D-conformers except for fucose which is an L-conformer.

EXAMPLE A

Synthesis of 8-Methoxycarbonyloctyl-2-acetamido-3-O-(2,3,4-tri-O-benzyl-α-L-fucopyranosyl) -6-O-benzyl-2-deoxy-β-D-glucopyranoside (Compound 1)

Step 1—Synthesis of p-Chlorophenyl 2,3,4-tri-O-benzyl-β-L-thiofucopyranoside

A 20 L three-necked round bottom flask, reflux condenser and 1000 mL addition funnel were dried and then cooled under a flow of nitrogen. The flask was charged with 1000 g of L-fucose, 500 g of anhydrous sodium acetate and 8000 mL of dry dichloroethane. The mixture was then heated with stirring to 50° C. The addition funnel was charged with 4000 mL (4×1000 mL) of acetic anhydride which was then added to the stirred, warm (50° C. to 55° C.) slurry in dropwise fashion at a rate that did not cool the reaction appreciably. Upon completion of the addition, the reaction mixture was stirred for 72 hours at 50° C. to 55° C. Aliquots were removed from the reaction mixture every 24 hours to check the progress of the reaction by tlc.

When the reaction was complete, 200 mL of water were added dropwise to the warm stirred mixture over 30 minutes and stirring was continued for 1 hour at this temperature. This converted the remaining acetic anhydride to acetic acid. The reaction mixture was then quenched into 3–4 volumes of water and the organic layer removed. The aqueous layer was extracted with 4 L dichloromethane and the combined organic layers backwashed three times with 2 L portions of water. The organic layers were dried over anhydrous sodium sulfate and concentrated under reduced pressure to approximately 5 L.

To the organic layer was added 925 g of p-chlorothiophenol. The organic layer was cooled with cold water. To the mixture of p-chlorothiophenol and fucose acetates was added 1.72 kg of boron trifluoride etherate in dropwise fashion. The mixture was then stirred for 6 hours (overnight is acceptable) allowing the reaction mixture to come to ambient temperature. A small aliquot was removed from the reaction mixture and quenched into sodium bicarbonate solution. Once carbon dioxide evolution ceases, the reaction was checked for completion by tlc. When complete, the whole reaction mixture was quenched into 1 L of saturated sodium bicarbonate and the organic layer separated after carbon dioxide evolution had finished. The organic layer was separated and air bubbled through this layer for 1 hour.

The separated organic layer was then dried over anhydrous sodium sulfate, filtered and the solvent evaporated. The residue was taken up in 1 L of dry methanol in a 2 L round bottom flask and treated with 1 g of freshly surfaced sodium. The reaction was kept under nitrogen for several hours and then checked by tlc for removal of the acetate groups. Upon completion, the reaction was neutralized with $H^+$ ion exchange resin, the reaction solution filtered and the solvent evaporated under reduced pressure. The residue was taken up in a minimum amount of hot isopropanol and 1060 g of the p-chlorophenyl-β-L-thiofucopyranoside crystallized from the solution after cooling overnight at 0° C.

p-Chlorophenyl-β-L-thiofucopyranoside was dissolved in 7 L of dry dimethylsulfoxide. To the solution was added 600 g of powdered KOH and the reaction mixture was stirred for 30 minutes. Benzyl chloride (1.275 L) was then added dropwise to the stirring solution and the mixture stirred overnight at room temperature. Tlc indicated incomplete reaction so an additional 300 g of powdered KOH was added to the reaction mixture followed 30 minutes later by 425 mL of benzyl chloride. The solution was stirred at room temperature until tlc indicated the reaction was complete. (If the reaction was not complete after 24 hours, additional powdered KOH was added followed by 200 mL of benzyl chloride). The reaction was quenched into several volumes of water and the reaction product extracted from the aqueous solution with methylene chloride. The organic layer was backwashed twice with water, dried and the solvent evaporated. The residue was then taken up in hot hexanes and p-chlorophenyl-2,3,4-tri-O-benzyl-β-L-thiofucopyranoside crystallized as the hexanes cooled. The precipitate was filtered and dried under vacuum to provide 1.3 kg of the title compound. Partial $^1$H-NMR (CDCl$_3$) data: δ=7.57 (m, 19H, aromatic), δ=4.99 (d, 1H), δ=4.65 (m, 5H), δ=4.55 (d, 1H, $J_{1,2}$9.5 Hz), δ=3.98 (t, 1H), δ=3.55 (m, 3H), δ=1.26 (d, 3H, $J_{5,6}$6.2 Hz, H-6).

Step 2—Synthesis of 8-Methoxycarbonyloctyl-2-acetamido-4,6-di-benzylidene-2-deoxy-β-D-glucopyranoside A 20 L glass reactor was charged with 8 L of dichloroethane, 1 L of acetic anhydride and 1 kg of anhydrous sodium acetate. To the stirring mixture was added 1 kg of glucosamine hydrochloride and the mixture was brought to reflux. A further 3.5 L of acetic anhydride was added dropwise to the refluxing solution over 3 to 4 hours and the solution maintained at reflux for 36 hours. During line last hour of reflux, 200 mL of water was added dropwise to the solution. The reaction was then cooled and added to 35 L of ice-water in a 50 L stirred reactor. The organic layer was removed and then washed a second time with an additional 20 L of water. The organic layer was dried over anhydrous sodium sulfate, filtered, and saturated with anhydrous gaseous HCl for 2 hours. The reaction was allowed to sit for 6 days being saturated with HCl for 1 hour every second day. 2-Acetamido-2-deoxy-3,4,6-tri-O-acetyl-β-D-glucopyranosyl chloride was isolated by quenching the reaction mixture into ice cold sodium bicarbonate solution. The organic layer was dried over anhydrous sodium sulfate and evaporated to a brown solid.

Four hundred grams of 2-acetamido-2-deoxy-3,4,6-tri-O-acetyl-β-D-glucopyranosyl chloride was dissolved in 2 L of anhydrous dichloromethane containing 200 g of activated molecular sieves. 8-Methoxycarbonyloctanol (266 g) was charged to the reaction mixture along with 317 g of mercuric cyanide. The solution was stirred rapidly at room temperature for 24 hours. After checking for reaction completion by tlc, the reaction mixture was filtered through a Buchner funnel containing silica and the organic layer was washed twice with water, twice with a 5% solution of potassium iodide and twice with a saturated solution of sodium bicarbonate. The solution was dried over anhydrous sodium sulfate and evaporated to dryness. The residue was taken up in anhydrous methanol and treated with 1 g of freshly cut sodium and then stirred at room temperature overnight. The solution of 8-methoxycarbonyloctyl 2-acetamido-2-deoxy-β-D-glucopyranoside was neutralized with an acid ion exchange resin, filtered and the solvent evaporated to yield 218 g after crystallization from isopropanol/diisopropyl ether.

Two hundred grams of 8-methoxycarbonyloctyl 2-acetamido-2-deoxy-β-D-glucopyranoside were dissolved in 1.2 L of anhydrous dimethylformamide and treated with 169 mL of dimethoxytoluene (benzaldehyde dimethyl acetal) and 1 to 2 g of p-toluenesulfonic acid. The reaction was stirred and heated to 40° C. for 5 h, then checked for completion by tlc. When the reaction was complete, the mixture was neutralized with triethylamine and quenched into several volumes of ice water. The product was extracted into dichloromethane and the organic solution backwashed several times with water. The organic solution was dried over anhydrous sodium sulfate, evaporated to dryness and taken up in hot isopropanol. After cooling, 8-methoxycarbonyloctyl-2-acetamido-4,6-O-benzylidene-2-deoxy-β-D-glucopyranoside precipitated. The precipitate was collected by filtration and dried to yield 106 g of product. Partial $^1$H-NMR (CDCl$_3$) data: δ=7.41 (m, 5H, aromatic), δ=6.11 (d, 1H, NH), δ=5.5 (s, 1H, CH), δ=4.63 (d, 1H, H-1, $J_{1,2}$7.4 Hz), δ=2.29 (t, 2H), δ=1.99 (s, 3H, Ac), δ=1.58 (m, 4H), δ=1.29 (bs, 8H).

Steps 3 and 4 provide an alternative synthesis for the preparation of 8-methoxycarbonyloctyl-2-acetamido-4,6-di-benzylidene-2-deoxy-β-D-glucopyranoside.

Step 3—Synthesis of 8-Methoxycarbonyloctyl-2-acetamido-2-deoxy-β-D-glucopyranoside Trimethylsilyl trifluoromethanesulfonate (2.5 mL, 12.8 mmol) in dichloromethane (5 mL) was added in portions over a period of 30 minutes to a cooled (0° to −5° C.) suspension of 2-acetamido-2-deoxy-1,3,4,6-tetra-O-acetyl-β-D-glucopyranoside (10 g, 25.7 mmol), CaSO$_4$ (20 g pulverized) and 8-methoxycarbonyloctanol (5.8 g, 30.8 mmol) in dichloromethane (50 mL) under nitrogen. Stirring was continued for 15 hours at room temperature by which time tlc showed complete consumption of the starting material and appearance of a new spot at higher Rf (ethyl acetate: hexane: methanol; 6:4:1). The reaction mixture was neutralized with sodium bicarbonate (30 g) and stirred for 0.5 hours. Sodium methoxide in methanol (1M) was added to maintain the pH at 9–9.5. The reaction mixture was stirred for 3 to 5 hours at room temperature, filtered and neutralized with IR-120 ($H^+$) ion exchange resin to maintain pH 7. The resin was removed by filtration and the solvent evaporated. Hexane (100 mL) was added to the residue and the mixture was stirred at 50° C. for 1 hour and then cooled to room temperature. As much hexanes as possible were decanted (the liquid was yellow in color) and the solids were re-evaporated to dryness. The residue was placed under high vacuum for 15 hours to provide 7.5 g of the title compound (yield 75%) as a solid having an Rf 0.40 (ethyl acetate: methanol; 4:1).

Step 4—Synthesis of 8-Methoxycarbonyloctyl-2-acetamido-4,6-di-O-benzylidene-2-deoxy-β-D-glucopyranoside To a stirred solution 8-methoxycarbonyloctyl-2-acetamido-2-deoxy-β-D-glucopyranoside (10 g, 25.6 mmol) in a mixture of anhydrous acetonitrile: dimethylformamide (100 mL, 9:1) was added benzaldehyde dimethyl acetal (4.8 mL, 31.9 mmol) and p-toluene sulfonic acid (50 mg). The mixture was stirred until all the starting material was consumed (about 24 h). The solution was then neutralized by adding 1 mL of triethylamine until a pH of 7–7.5 was attained. The solution was evaporated and then co-evaporated with toluene (200 mL) twice to dryness. The residue was dissolved in a solution of methanol (80 mL) and isopropanol (20 mL) by heating to 65°–70° C. with stirring and the resulting solution was allowed to cool to room temperature and stirring was continued for 1 hour. The solution was then filtered and washed with cold methanol (–20° C.) to provide 8.5 g (yield 69.4%) of the title compound having an Rf 0.85 (ethyl acetate:methanol; 4:1).

Step 5—Synthesis of 8-Methoxycarbonyloctyl-2-acetamido-3-O-(2,3,4-tri-O-benzyl-α-L-fucopyranosyl) -4,6-O-benzylidene-2-deoxy-β-D-glucopyranoside (Compound 3)

Dimethylformamide (8.1 mL, 104.3 mmol) and tetraethyl-ammonium bromide (2.2 g, 10.4 mmol) were added to a suspension of cupric bromide (11.6 g, 52.1 mmol) and 4A molecular sieves (20 g) in dry dichloromethane (10 mL). After stirring the dark green mixture for 0.5 hours at room temperature, a solution of 8-methoxycarbonyloctyl-2-acetamido-4, 6-di-O-benzylidene-2-deoxy-β-D-glucopyranoside, compound 2, (5 g, 10.4 mmol) in dichloromethane (10 mL) and of p-chlorophenyl 2,3,4-tri-O-benzyl-β-L-thiofucopyranoside, compound 1, (8.5 g, 15.6 mmol) in dry dichloromethane (5 mL) were added by syringe. After stirring for 15 hours, the reaction mixture was diluted with dichloromethane (500 mL), filtered through celite and washed with a 5% solution of EDTA (3×500 mL) until colorless. The solution was dried over anhydrous sodium sulfate and the solvent evaporated. The residue was passed through a silica gel column (70–230 mesh) using hexane:ethyl acetate (2:1) and (1:1) as the eluant. Fractions containing the title compound were pooled and the solution evaporated. The resulting product was crystallized from hot isopropanol to provide 7 g (74.9% yield) of the title compound.

Alternatively, the product, after work-up, can be directly crystallized from isopropanol in 85–90% yield without column chromatography if large excess of donor is avoided. Partial 1H-NMR ($CDCl_3$) data: δ=7.49–7.20 (m, 20H, aromatic), δ=5.67 (d, J 7.5 Hz, NH), δ=5.49 (s, 1H, $C_6CHO$), δ=4.65 (d, 1H, $J_{gem}$ 12.5 Hz, $C_6H_5CHH$), δ=4.57 (d, 1H, $J_{gem}$ $C_6H_5CHH$), δ=5.07 (d, 1H, $J_{1',2}$3.2 Hz, H-1'), δ=3.65 (s, 3H, $OCH_3$), δ=2.29 (t, 2H, J 7.5 Hz, $CH_2COO$), δ=1.64 (s, 3H, $NHC(O)CH_3$), δ=0.81 (d, 3H, $J_{5',6}$6.5 Hz, H-6').

Step 6—Synthesis of 8-Methoxycarbonyloctyl-2-acetamido-3—O-(2,3,4-tri-O-benzyl-α-L-fucopyranosyl)-6-O-benzyl-2-deoxy-β-D-glucopyranoside (Compound 1)

A mixture of 8-methoxycarbonyloctyl-2-acetamido-3-O-(2,3,4-tri-O-benzyl-α-L-fucopyranosyl)-4,6-O-benzylidene-2-deoxy-β-D-glucopyranoside (20 g, 22.3 mmol), sodium cyanoborohydride (14 g), 3A molecular sieves (20 g), and a few crystals of methyl orange in tetrahydrofuran (500 mL) was stirred at 0° C. under nitrogen. Diethylether saturated with hydrogen chloride was added until the color of the indicator turned red and gas evolution occurred. The reaction was monitored for completion by tlc (1:1 hexane:ethyl acetate). The reaction mixture was then diluted with dichloromethane (500 mL) and poured into aqueous sodium hydrogen carbonate (500 mL), dried over anhydrous sodium sulfate, and the solvent evaporated. The crude product was dissolved in methanol:dichloromethane (1:1) and deionized with mixed-bed ion-exchanger MB-1. The resin was washed thoroughly with methanol:dichloromethane (1:1) and the solution evaporated to leave a foam which was then chromatographed on silica gel (230–400 mesh) using hexane:ethyl acetate (1:1) as the eluant. The appropriate fractions were collected and the solvent was removed. The residue was then crystallized from hot isopropanol to provide for 14 g (70.2% yield) of compound 1.

Alternatively, the product, after work-up, can be crystallized directly from isopropanol in 75–80% yield without any column chromatography.

Partial $^1$H-NMR ($CDCl_3$) data: δ=7.38–7.20 (m, 20H, aromatic), δ=4.95 (d, 1H, $J_{1',2}$3.2 Hz, H-1'), δ=4.89 (d, 1H, $J_{gem}$11.5 Hz, $C_6H_5CHH$), δ=3.62 (s, 3H, $OCH_3$), δ=2.25 (t, 2H, J 7.5 Hz, $CH_2COO$), δ=1.63 (s, 3H, $NHC(O)CH_3$), δ=1.11 (d, 3H, $J_{5',6}$6.5 Hz, H-6').

Step 7 provides an alternative synthesis for compound 1.

Step 7—Synthesis of 8-Methoxycarbonyloctyl-2-acetamido-3-O-(2,3,4-tri-O-benzyl-α-L-fucopyranosyl)-6-O-benzyl-2-deoxy-β-D-glucopyranoside (Compound 1)

To a 1 L jacketed reactor equipped with magnetic stirrer under nitrogen was added 8-methoxycarbonyloctyl-2-acetamido-3-O-(2,3,4-tri-O-benzyl-α-L-fucopyranosyl)-4, 6-O-benzylidene-2-deoxy-α-D-glucopyranoside, (50.05 g, 0.06 mol), borane trimethylamine complex (20.6 g, 0.28 mol), and tetrahydrofuran (500 mL). The reaction mixture was cooled to –10° C. and stirred vigorously. Anhydrous aluminum chloride (137.0 g) was then added to the reaction vessel. Once all the aluminum chloride was added, the temperature of the reactor was maintained at –10° C. and trifluoroacetic acid (21.5 mL, 0.28 mol) was added dropwise while monitoring the temperature of the reaction mixture. Completion of the reaction was monitored by tlc (1:1 hexane:ethyl acetate). Once the reaction was complete, the mixture was transferred to a 6 L separatory funnel containing 1 L dichloromethane, ice and 1 L of 5% $H_2SO_4$. The organic layer was transferred to a 2 L Erlenmeyer flask and the aqueous layer was extracted with 200 mL of dichloromethane. The combined dichloromethane layer was washed with ice cold 6% sodium bicarbonate (200 g). The solution was then filtered using a filtration flask (2 L) on a Buchner funnel (7.5 cm) and rinsed with dichloromethane (500 mL). The filtrate was evaporated to dryness to provide a pale yellow solid. The crude product was purified by chromatography using 70–230 mesh silica gel and a 3" HPLC column packed with dichloromethane. The column was eluted with hexane:ethyl acetate (2:1) to remove all excess borane complex. Once all the yellow colored material had eluted, the column was then eluted with hexane:ethyl acetate (1:1). The pure fractions were concentrated to a white solid on a 20 L rotary evaporator and dried under vacuum to provide 3.3 g (67% yield) of compound 1.

EXAMPLE B

Synthesis of Compound 2

5-Acetamido-4,7,8,9-tetra-O-acetyl-3,5-dideoxy-α-D-glycero-D-galacto-2-nonulopyranosylonate)-(2→3)-O-(1,2,4,6-tetra-O-acetyl-β-D-galactopyranose, compound 15 in Ratcliffe, et al.[1] was converted to its anomeric hydroxy compound by reaction with 2 equivalents of hydrazine acetate in DMF at room temperature for 2 to 5 hours. The hydroxy compound was then converted into its trichloroacetimidate derivative by reaction with 2–5 equivalents of trichloroacetonitrile using 0.2 to 0.5 of DBU in dichloromethane at from 0° C. to room temperature.

EXAMPLE 1

Synthesis of 8-Methoxycarbonyloctyl(benzyl 5-acetamido-4,7,8,9-tetra-O-acetyl-3,5-di-deoxy -α-D-glycero-D-galacto-2-nonulopyranosylonate)-(2→3)-O-(2,4,6-tri-O-acetyl-α-D-galactopyranosyl) -(1→4) -O-[2,3,4-tri-O-benzyl-α-L-fucopyranosyl-(1→3)-O-]-2-acetamido-2-deoxy-6-O-benzyl-β-D-glucopyranoside (compound 3)

The synthesis described in this example is illustrated in FIG. 1.

A solution of disaccharide acceptor 1 (4.0 g) and sialylgalactose imidate donor (2) (6.5 g) in CH$_2$Cl$_2$: diethylether (1:1, 60 mL) was cooled to about −30° C. Molecular sieves (pulverized 4A, 12.0 g) were added and the reaction mixture was stirred for 10 minutes at about −30° C. Boron trifluoride etherate was added to the solution dropwise for 45 minutes and the solution was then allowed to warm to −10° C. The reaction mixture was then stirred for an additional 0.5 hours. The completion of the reaction was monitored by tlc using hexane:ethyl acetate:ethanol (60:40:10) as the eluant. After completion, the reaction mixture was neutralized with triethylamine (1.0 mL), filtered and evaporated. The syrup was purified by chromatography on Iatrobeads using hexane:ethyl acetate:ethanol:dichloromethane (60:40:5:5) as the eluent to provide for the title compound (6.0 g, 87.2%) as a foam.

EXAMPLE 2

Synthesis of 8-Methoxycarbonyloctyl-(5-acetamido-4,7,8,9-tetra -O-acetyl-3,5 -di-deoxy-α-D-glycero-β-galacto-2-nonulopyranosylonic acid)-(2→3)-O-(2,4,6-tri-O-acetyl-β-D -galactopyranosyl)-(1→4)-O-[α-L-fucopyranosyl-(1→3)-O-]-2-acetamido-2-deoxy-β-D-glucopyranoside (compound 4)

The synthesis described in this example is illustrated in FIG. 1.

Blocked sialyl Lewis$^x$-OR tetrasaccharide produced in Example 1 above (6.8 g) was dissolved in methanol (80.0 mL) and 5% palladium on carbon added to it. Hydrogenation of the benzyl ether groups was carried out by bubbling hydrogen (H$_2$) through the solution at atmospheric pressure and room temperature. After 1.5 hours, tlc showed complete consumption of starting material using hexane:ethyl acetate:ethanol (60:40:10) as the eluent and the product was eluted with dichloromethane:methanol (80:20) for the appearance of the product. The catalyst was filtered on a pad of celite and purified by chromatography on Iatrobeads using dichloromethane:methanol (80:20) as eluent to provide for the title compound (4.36 g, 86%).

EXAMPLE 3

Synthesis of 8-Methoxycarbonyloctyl-(5-acetamido-3,5-di-deoxy-α-D-glycero-D-galacto -2-nonulopyranosylonic acid)-(2→3)-O-β-D-galactopyranosyl)-(1→4)-O-[α-L-fucopyranosyl-(1→3)-O-]-2-acetamido -2-deoxy-β-D-glucopyranoside (compound 5)

The synthesis described in this example is illustrated in FIG. 1.

Compound 4 (4.36 g) was dissolved in sodium methoxide/methanol solution (40.0 mL, 0.5M solution) at 0° C. and stirred at room temperature. After stirring for 3 hours at room temperature, the reaction mixture was neutralized with IRC-120 (H$^+$) ion exchange resin. After filtering and evaporating, the product was purified by chromatography on Iatrobeads using isopropanol:water:ammonia (70:30:5) as eluent to provide for the title compound (3.06 g, 90%).

Figure 2:
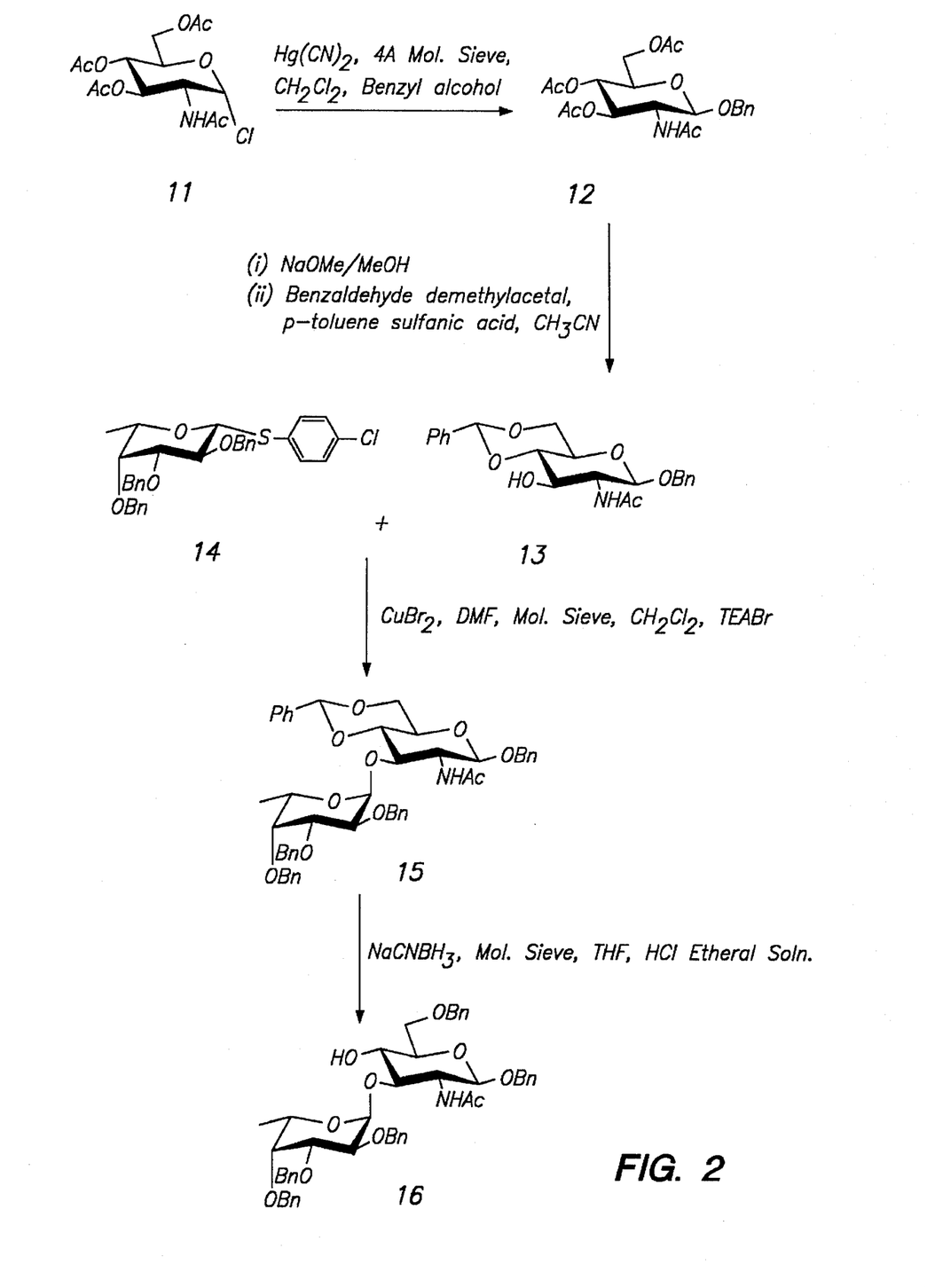
FIGS. 2 and 3 illustrate a preferred reaction scheme which can be used to obtain the sialyl Lewis$^x$-OH compounds described herein.
Figure 3:
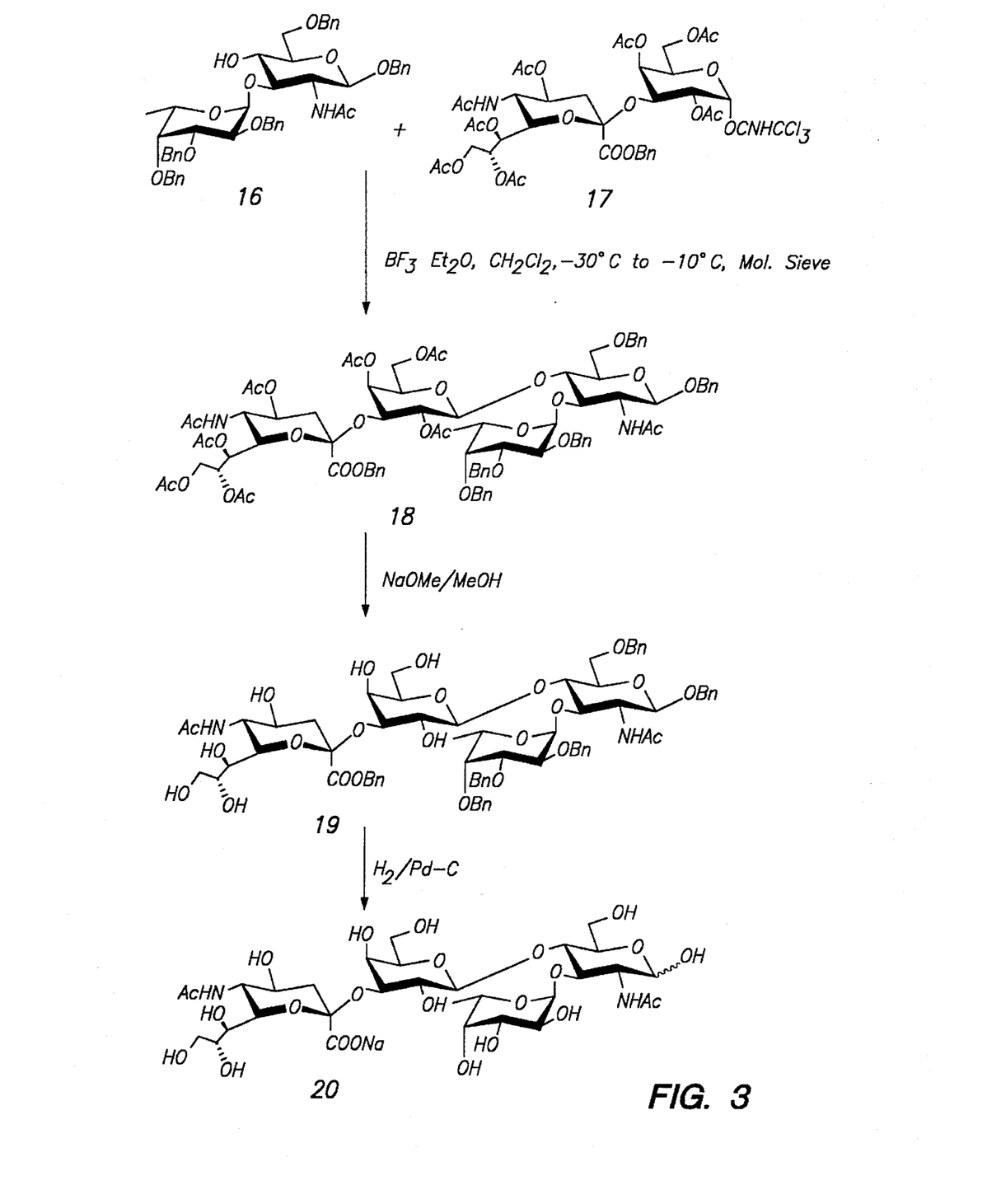

The synthesis of sialyl Lewis$^x$-OH depicted in Examples 4–10 below is illustrated in FIGS. 2 and 3.

EXAMPLE 4

Synthesis of Benzyl-2-acetamido-3,4,6-tri-O-acetyl-2-deoxy-β-D-glucopyranoside (compound 12)

Chloro-2-acetamido-3,4,6-tri-O-acetyl-2-deoxy-α-L-glucopyranoside (compound 11—prepared as in U.S. Ser. No. 08/343,020 as compound 2B therein) (20.4 g, 55.77 mmol), benzyl alcohol (6.93 mL, 1.2 eq.) and molecular sieves (4A, 10.0 g) was stirred in dichloromethane (160 mL) for 0.5 hours under nitrogen. Mercuric cyanide (14.1 g, 1 eq.) was added to the reaction mixture and then the system was stirred for 15 hours at room temperature. The reaction mixture was then diluted with dichloromethane (1.0 L) and filtered. Filtrate was washed with aqueous potassium iodide (2×1.0 L) and water (2×1.0 L), dried over anhydrous sodium sulfate and then filtered. The solvent was then evaporated to provide for a syrup which was dissolved in ethyl acetate at 65° C. and hot filtered. The product was recovered by crystallization upon cooling the hot solution to room temperature to provide for 16.9 g of the title compound.

EXAMPLE 5

Synthesis of Benzyl-2-acetamido-4,6-O-benzylidene-2-deoxy-β-D-glucopyranoside (compound 13)

Benzyl-2-acetamido-3,4,6-tri-O-acetyl-2-deoxy-β-D-glucopyranoside (compound 12) (16.9 g) was dissolved in methanol (100 mL) and then a catalytic amount of sodium methoxide (0.5M) in methanol was added. The system was stirred for 5 hours at room temperature; the solution was neutralized with IR-120 (H⁺) resin; and then the solvent evaporated. The resulting product was crystallized by dissolving in hot methanol and cooling to 0° C. to provide for 9.94 g of the 3,4,6-trihydroxy compound as a solid. This product was then directly converted into the title compound (i.e., the 4,6-O-benzylidine derivative) by reacting with benzaldehyde dimethylacetal (9.34 mL) and p-toluene sulfonic acid (100 mg) in acetonitrile (150 mL). The title compound, 10 g, was obtained as a solid.

EXAMPLE 6

Synthesis of Benzyl-2-acetamido-3-O-(2,3,4-tri-O-benzyl-α-L-fucopyranosyl)-4,6-O-benzylidene-2-deoxy-β-D-glucopyranoside (compound 15)

DMF (27.0 mL) and tetraethylammonium bromide (7.9 g, 1 eq.) were added to a suspension of cuptic bromide (42.0 g, 5.0 eq.) and 4A molecular sieves (30.0 g) in dry dichloromethane (37.0 mL). After stirring the dark green mixture for 0.5 hours at room temperature, a solution of benzyl-2-acetamido-4,6-O-benzylidene-2-deoxy-β-D-glucopyranoside (compound 14) (15.0 g) in dichloromethane (100 mL) and of p-chlorophenyl-2,3,4-tri-O-benzyl-β-L-thiofucopyranoside (31.63 g, 1.5 eq.— compound 1 of U.S. patent application Ser. No. 08/343,020) in 50 mL of dichloromethane was added.

After stirring the reaction mixture for 7 hours at room temperature, the mixture was diluted with dichloromethane (500 mL) and filtered. The solids collected by the filtering were further washed with dichloromethane (500 mL) and the dichloromethane solutions were combined and then washed with a 5% solution of EDTA (5×1 L) until colorless. The solution was dried over anhydrous sodium sulfate and the solvent evaporated. The residue was purified by chromatography on silica gel using dichloromethane:methanol (98:2) as the eluent to provide for the title compound (26.82 g, 87.5%) as a white solid.

EXAMPLE 7

Synthesis of Benzyl-2-acetamido-3-O-(2,3,4-tri-O-benzyl-α-L-fucopyranosyl)-6-O-benzyl-2-deoxy-β-D-glucopyranoside (compound 16)

A mixture of benzyl-2-acetamido-3-O-(2,3,4-tri-O-benzyl-α-L-fucopyranosyl)-4,6-O-benzylidene-2-deoxy-β-D-glucopyranoside (compound 15) (26.0 g), sodium cyanoborohydride (50.0 g), 3A molecular sieves (26.0 g) and a few crystals of methyl orange in tetrahydrofuran (600 mL) was stirred at 0° C. under nitrogen. Diethylether saturated with hydrogen chloride was then added until the color of the indicator turned red and gas evolution occurred. The reaction was monitored for completion by tlc (1:1 hexane:ethyl acetate). The reaction was then diluted with dichloromethane (1.0 L) and poured into an aqueous saturated sodium hydrogen carbonate solution (1.0 L). The organic layer was filtered, dried over anhydrous sodium sulfate and the solvent evaporated. The crude product was dissolved in methanol:dichloromethane (1:1) and deionized with mixed-bed ion-exchanger MB-1 available from Aldrich Chemical Company, Milwaukee, Wis., USA. The resin was washed thoroughly with a mixture of methanol and dichloromethane (1:1) and the solvent evaporated to leave a foam which was then chromatographed on silica gel using hexane:ethyl acetate (3:2) as the eluent. The fractions containing product were pooled, the solvent evaporated and the residue crystallized from isopropanol to yield the title compound (28.0 g).

EXAMPLE 8

Synthesis of Benzyl-(benzyl-5-acetamido-4,7,8,9-tetra-O-acetyl -3,5-dideoxy-α-D-glycero-D-galacto-2-nonulopyranosylonate-(2→3)-O-(2,3,6-tri-O-acetyl-β-D-galactopyranosyl) -(1→4)-O-[2,3,4-tri-O-benzyl-α-L-fucopyranosyl-(1→3)-O-]-2-acetamido-6-O-benzyl-2-deoxy-β-D-glucopyranoside (compound 18)

A. 5-Acetamido-4,7,8,9-tetra-O-acetyl-3,5-dideoxy-α-D-glycero-D-galacto-2-nonulopyranosylonate) -(2→3)-O-(1, 2,4,6-tetra-O-acetyl-β-D-galactopyranose, compound 15 in Ratcliffe, et al.[1] was converted to its anomeric hydroxy compound by reaction with 2 equivalents of hydrazine acetate in DMF at room temperature for 2 to 5 hours. The hydroxy compound was then converted into its imidate derivative by reaction with 2–5 equivalents of trichloroacetonitrile using 0.2 to 0.5 of DBU in dichloromethane at from 0° C. to room temperature to provide for compound 17.

B. To a mixture of benzyl-2-acetamido-3-O-(2,3,4-tri-O-benzyl-α-L-fucopyranosyl) -6-O-benzyl-2-deoxy-β-D-glucopyranoside (compound 16) (2.7 g), the imidate of step A above (compound 17) (5.0 g, 1.5 eq.) and pulverized 4A molecular sieves (7.0 g) in a mixture of dichloromethane:diethyl ether (30 mL, 1:1) was added boron trifluoride etherate solution (1.2 mL, 2 eq.) dropwise at –30° C. under nitrogen and the reaction mixture was then stirred at this temperature for 1.5 hours. The reaction mixture was warmed to –10° C. over 0.5 hours and stirred for an additional hour at this temperature.

Triethylamine was added to neutralize any acid and the reaction solution was diluted with 500 mL of dichloromethane. The resulting solution was filtered, washed with saturated sodium bicarbonate solution (2×500 mL) and water (2×500 mL), dried over anhydrous sodium sulfate, filtered and evaporated to dryness. The crude mass was purified by chromatography on Iatrobeads using hexane:ethyl acetate:ethanol:dichloromethane (6:4:1:1) as the eluent to provide for the title compound (4.37 g, 81%).

EXAMPLE 9

Synthesis of Benzyl-(benzyl-5-acetamido-3,5-dideoxy-α-D-glycero-D-galacto-2-nonulopyranosylonate -(2→3)-O-(β-D-galactopyranosyl)-(1→4)-O-[2,3,4-tri-O-benzyl-α-L-fucopyranosyl-(1→3) -O-]-2-acetamido-6-O-benzyl-2-deoxy-β-D-glucopyranoside (compound 19)

Benzyl-(benzyl-5-acetamido-4,7,8,9-tetra-O-acetyl-3,5-dideoxy-α-D -glycero-D-galacto-2-nonulopyranosylonate-(2→3)-O-(2,3,6-tri-O-acetyl-β-D-galactopyranosyl)-(1→4) -O-[2,3,4-tri-O-benzyl-α-L-fucopyranosyl-(1→4)-O-]-2-acetamido-6-O-benzyl-2-deoxy-β-glucopyranoside (compound 18) (4.0 g) was dissolved in methanol (20 mL) and sodium hydroxide (0.2M, 30.0 mL) was added at 0° C. and stirred for 15 hours. The reaction solution was then neutralized with IRC-120 (H⁺) ion exchange resin, filtered and evaporated to obtain the title compound (2.6 g).

EXAMPLE 10

Synthesis of O-(5-acetamido-3,5-dideoxy-α-D-glycero-D-galacto-2-nonulopyranosylonate -(2→3)-O-(β-D-galactopyranosyl)-(1→4)-O-[α-L-fucopyranosyl-(1→3)-O-]-2-acetamido-2-deoxy-β-D-glucopyranoside (compound 20)

Benzyl-(benzyl-5-acetamido-3,5-dideoxy-α-D-glycero-D-galacto-2-nonulopyranosylonate -(2→3)-O-(β-D- galactopyranosyl)-(1→4)-O-[2,3,4-tri-O-benzyl-α-L-fucopyranosyl-(1→3)-O-]-2-acetamido-6-O-benzyl-2-deoxy-β-D-glucopyranoside (compound 19) (2.6 g) was dissolved in methanol (30.0 mL) and 5% palladium on carbon (3.0 g) was added. The reaction system was then hydrogenated under one atmosphere of hydrogen for 7 hours. Afterwards, the reaction system was filtered and the solids washed thoroughly with methanol. The solutions were combined and the solvent evaporated to provide a syrup. The syrup was dissolved in 20 mL of water and then filtered through a 0.22 micron filter and the solution was then lyophilized to provide for the title compound (1.61 g, 93%).

II. BIOLOGICAL RESULTS

Example 11 illustrate the anti-inflammatory properties of compounds disclosed herein.

EXAMPLE 11

Inhibition of DTH Inflammatory Response

DTH inflammatory responses were measured using the mouse footpad swelling assay as described by Smith and Ziola[13]. Briefly, groups of Balb/c mice (about 19–20 grams each) were immunized with 10 μg of the L111 S-Layer protein, a bacterial surface protein[14] from *Clostridium thermohydrosulfuricum* L111-69 which has been shown to induce a strong inflammatory DTH response or with 100 μg of the OVA antigen containing 20 μg of the adjuvant (DDA—dimethyldioctadecyl-ammonium bromide) which also induces a strong inflammatory DTH response. Seven days later, each group of mice was footpad-challenged with either 10 μg of L-111 S-Layer protein or with 20 μg of the OVA antigen (without adjuvant). The resulting inflammatory footpad swelling was measured with a Mitutoyo Engineering micrometer 24 hours after challenge.

To assess the effect of sialyl Lewis$^x$-Y compounds on the inflammatory DTH response, groups of mice received 100 μg of sialyl Lewis$^x$-O(CH$_2$)$_8$COOCH$_3$ or 2-N$_3$-sialyl Lewis$^x$-O-(CH$_2$)$_8$COOCH$_3$ (αNeu5Ac(2→3)βGal(1→4)-[α-L-Fuc(1→3)]-βGlc-2-N$_3$-O(CH$_2$)$_8$COOCH$_3$ which was injected as a solution into the tail vein, 5 hours after challenge. A control group was left untreated or received 100 μL of phosphate-buffered saline (PBS). The results of this experiment demonstrate that sialyl Lewis$^x$-O(CH$_2$)$_8$COOCH$_3$ and 2-N$_3$-sialyl Lewis$^x$-O-(CH$_2$)$_8$COOCH$_3$ possessed anti-inflammatory properties.

What is claimed is:

1. A process for the preparation of sialyl Lewis$^x$-Y compounds which process comprises:

(a) contacting a compound of formula I with at least a stoichiometric amount of a compound of the formula II in an inert diluent at from about −30° to about 0° C. to provide for a compound of formula III:

wherein each X is independently selected from the group consisting of —NHB and —NHC(O)R$^1$ where R$^1$ is alkyl of from 1 to 6 carbon atoms, alkaryl of from 7 to 12 carbon atoms, aryl of from 6 to 10 carbon atoms, alkheteroaryl, or heteroaryl; Y is selected from the group consisting of —OB, —OR, —SB, —SR, and —NHR; each B is independently a removable blocking group; B' is a removable blocking group selected from the group consisting of benzyl and substituted benzyl; and L is a leaving group;

(b) removing all of the B and B' removable blocking groups to provide for a compound of formula IV:

or a salt thereof wherein L and X are as defined above and Y' is selected from the group consisting of —OH, —OR, —SH, —SR, and —NHR, and (c) optionally converting the compound produced in (b) above to a pharmaceutically acceptable salt, wherein R is an aglycon of at least one carbon atom.

2. The process of claim 1 wherein Y is —NHR.
3. The process of claim 1 wherein Y is —OR.
4. The process of claim 1 wherein Y is —OH.
5. The process of claim 1 wherein Y is —NHR.
6. The process of claim 5 wherein Y is benzamido.

7. The process of claim 1 wherein X is —NHC(O)R' where $R^1$ is alkyl of from 1 to 6 carbon atoms, alkaryl of from 7 to 12 carbon atoms or aryl of from 6 to 10 carbon atoms.

8. The process of claim 7 wherein $R^1$ is aryl of from 6 to 10 carbon atoms.

9. The process of claim 8 wherein $R^1$ is phenyl.

10. The process of claim 7 wherein $R^1$ is alkaryl of from 7 to 12 carbon atoms.

11. The process of claim 10 wherein $R^1$ is benzyl.

12. The process of claim 1 wherein the compound of formula II is employed at from about 1.2 to about 1.5 equivalents relative to the compound of formula I.

* * * * *